US006921200B1

(12) United States Patent
Booysen et al.

(10) Patent No.: US 6,921,200 B1
(45) Date of Patent: Jul. 26, 2005

(54) IMAGING APPARATUS

(75) Inventors: Andre Booysen, Roodeport (ZA); Johannes Hermanus Potgieter, Midrand (ZA); Paul Van Looy, Randburg (ZA); Carlos Manuel de Seabra Sousa, Primrose (ZA); Andries Gerhardus Johannes Vermeulen, Moreletapark (ZA)

(73) Assignee: Lodox Systems (Proprietary) Limited, Gauteng (ZA)

( * ) Notice: Subject to any disclaimer, the term of this patent is extended or adjusted under 35 U.S.C. 154(b) by 0 days.

(21) Appl. No.: 09/936,152

(22) PCT Filed: Mar. 10, 2000

(86) PCT No.: PCT/IB00/00256

§ 371 (c)(1),
(2), (4) Date: Feb. 13, 2002

(87) PCT Pub. No.: WO00/53093

PCT Pub. Date: Sep. 14, 2000

(30) Foreign Application Priority Data

Mar. 10, 1999 (ZA) .............................................. 99/1927

(51) Int. Cl.[7] .............................................. H05G 1/30
(52) U.S. Cl. ........................ 378/205; 378/196; 378/98.8
(58) Field of Search ............................... 378/98.8, 205, 378/196, 97, 108, 10, 24, 44, 4, 19, 119, 62, 11, 116

(56) References Cited

U.S. PATENT DOCUMENTS

| 4,051,377 | A | * | 9/1977 | Kemner et al. ................ 378/16 |
| 4,179,100 | A | | 12/1979 | Sashin et al. |
| 6,057,552 | A | * | 5/2000 | Stettner et al. ......... 250/370.09 |
| 6,217,214 | B1 | * | 4/2001 | Cabral et al. ............... 378/196 |
| 6,445,767 | B1 | * | 9/2002 | Karellas ..................... 378/98.8 |
| 6,479,827 | B1 | * | 11/2002 | Hamamoto et al. ..... 250/370.11 |

FOREIGN PATENT DOCUMENTS

| DE | 3503 465 | 8/1985 |
| ZA | 93/8427 | 5/1994 |

* cited by examiner

*Primary Examiner*—Edward J. Glick
*Assistant Examiner*—Hoon Song
(74) *Attorney, Agent, or Firm*—Scully, Scott, Murphy & Presser

(57) ABSTRACT

X-ray imaging apparatus is provided for generating a composite image of a subject by moving a radiation source (12) and a camera array (122) relative to the subject. A drive mechanism (22) generates clock signals which are used to synchronize the operation of the camera array with the movement thereof, and the composite image data which is generated is stored for display and further signal processing. Control means move the radiation source (12) and the camera array (122) according to the intensity of the imaging beam.

10 Claims, 12 Drawing Sheets

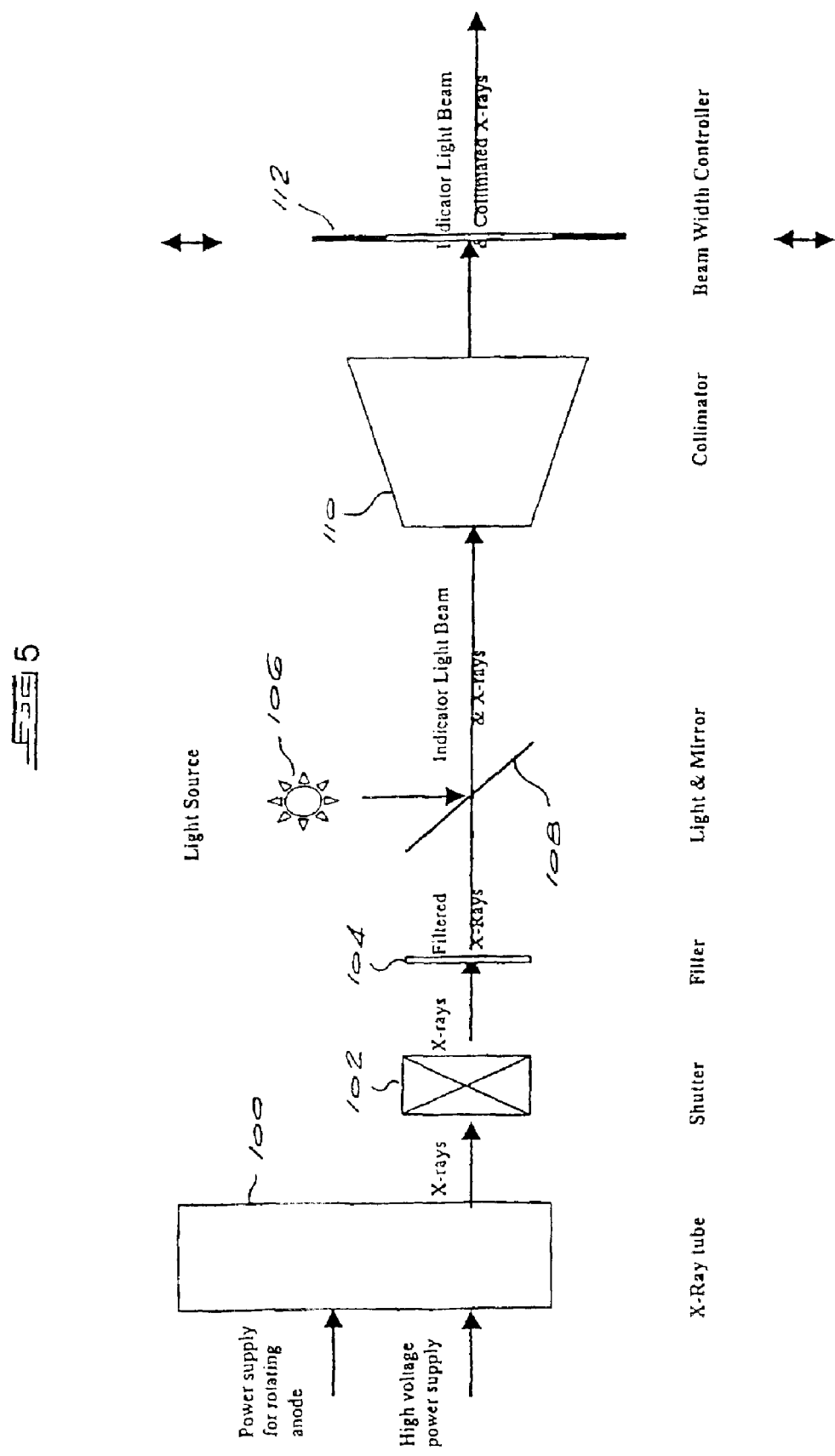

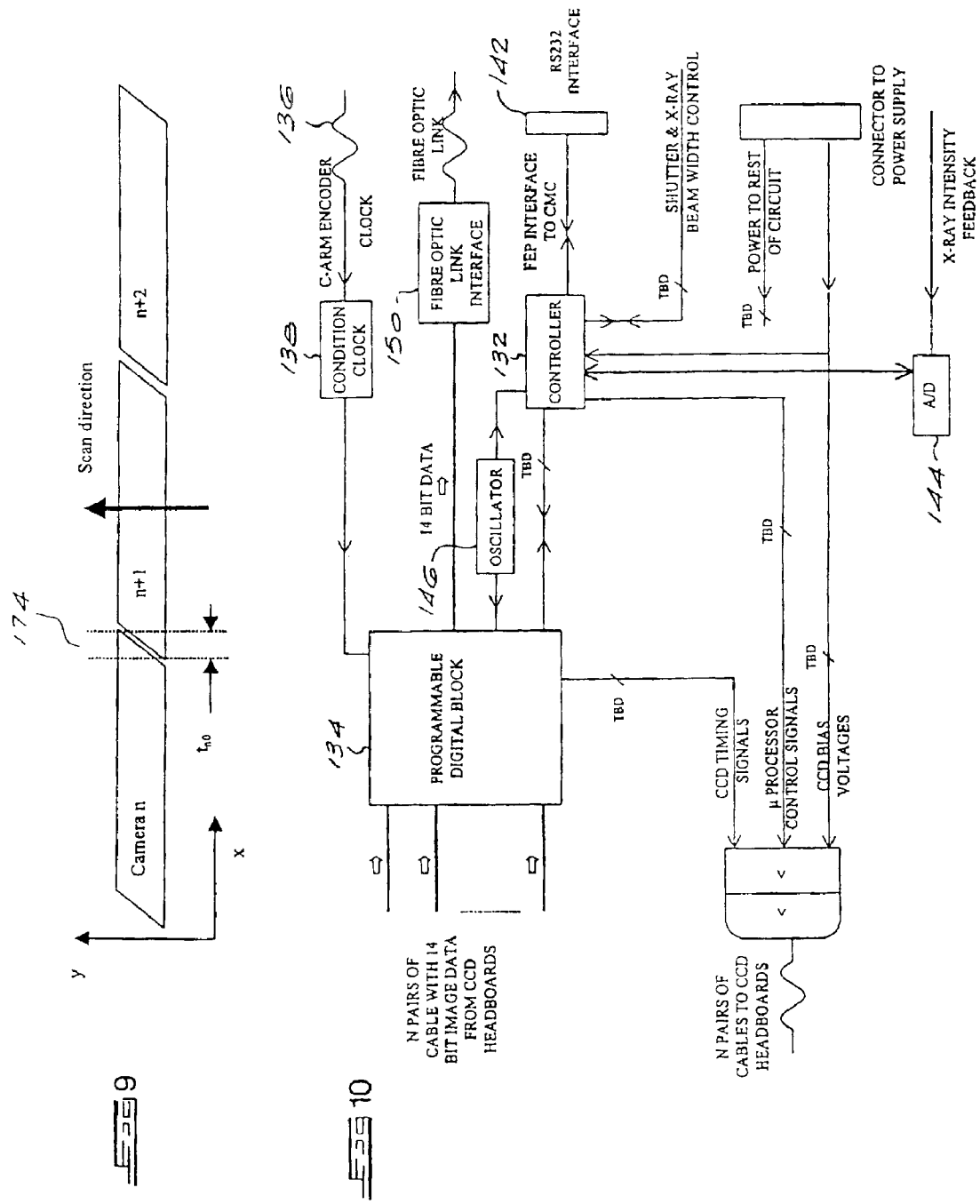

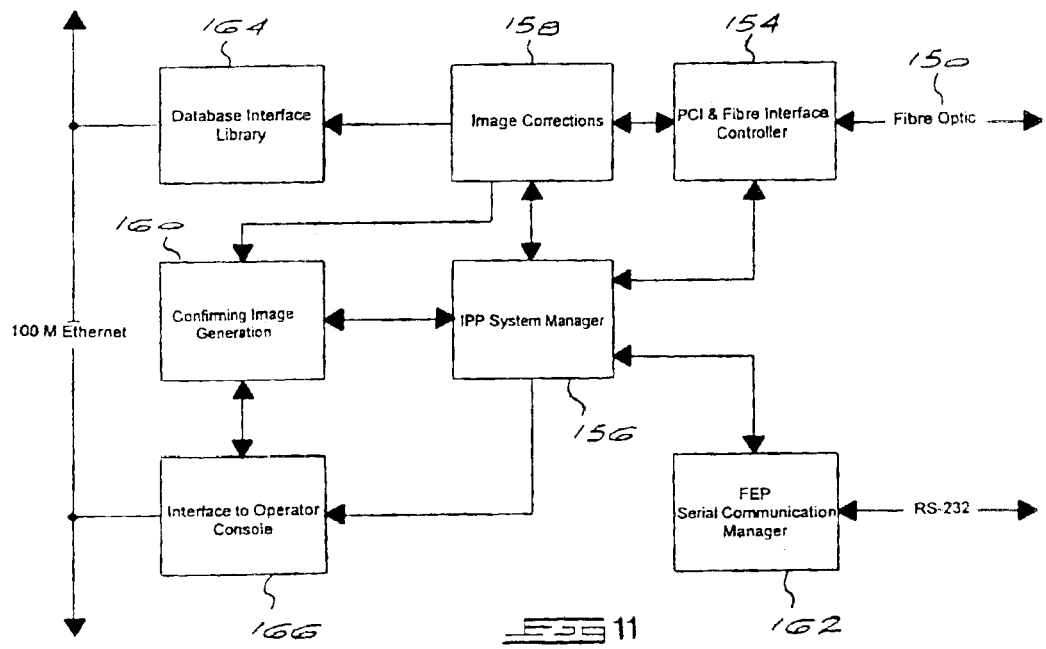
Fig. 11
Fig. 14a
Fig. 14b
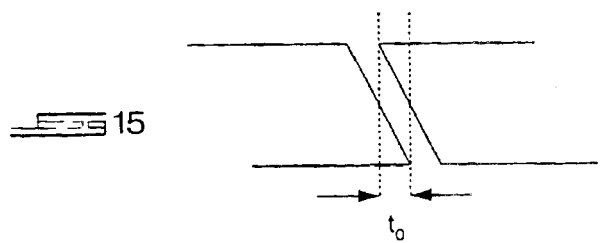
Fig. 15

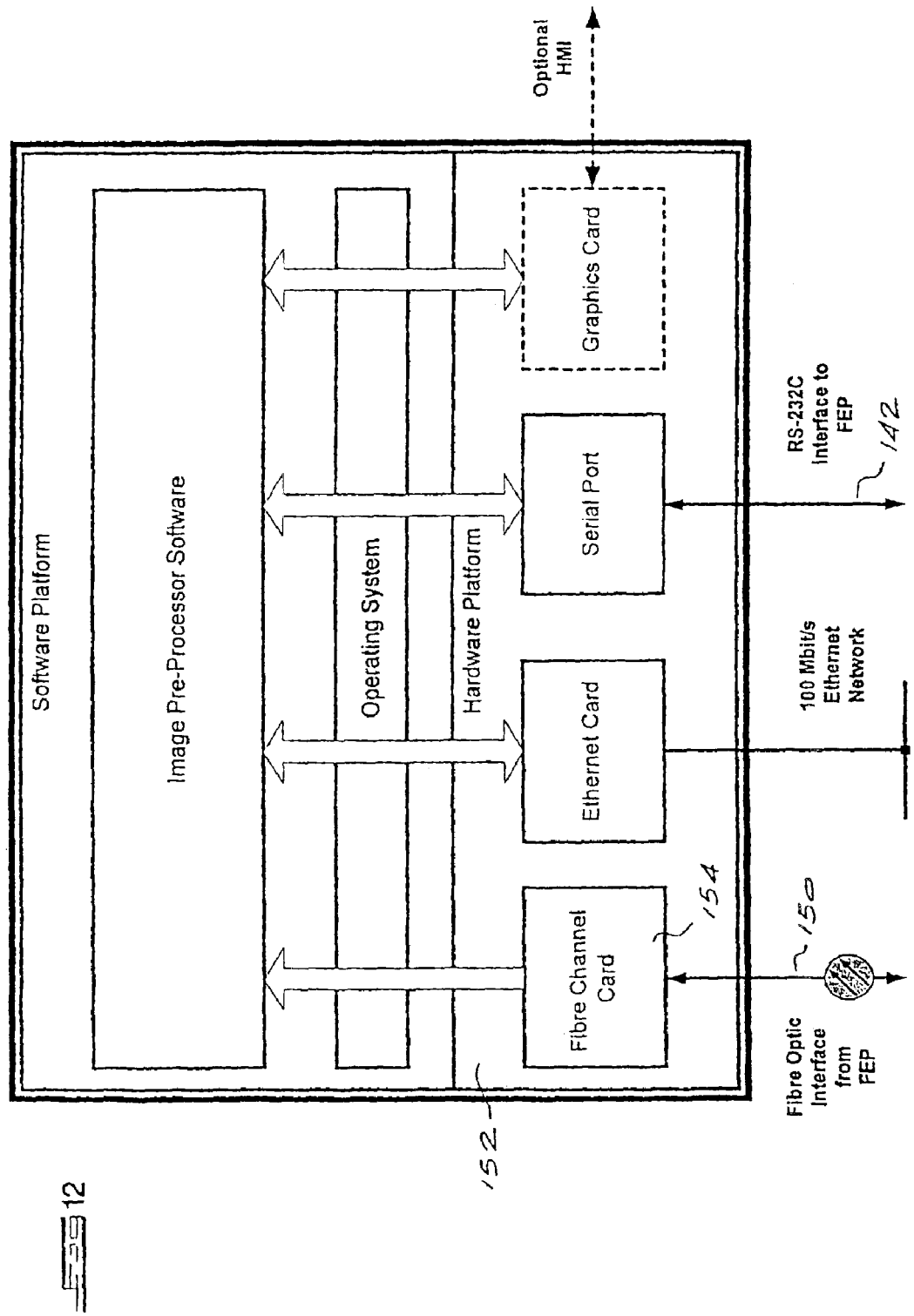

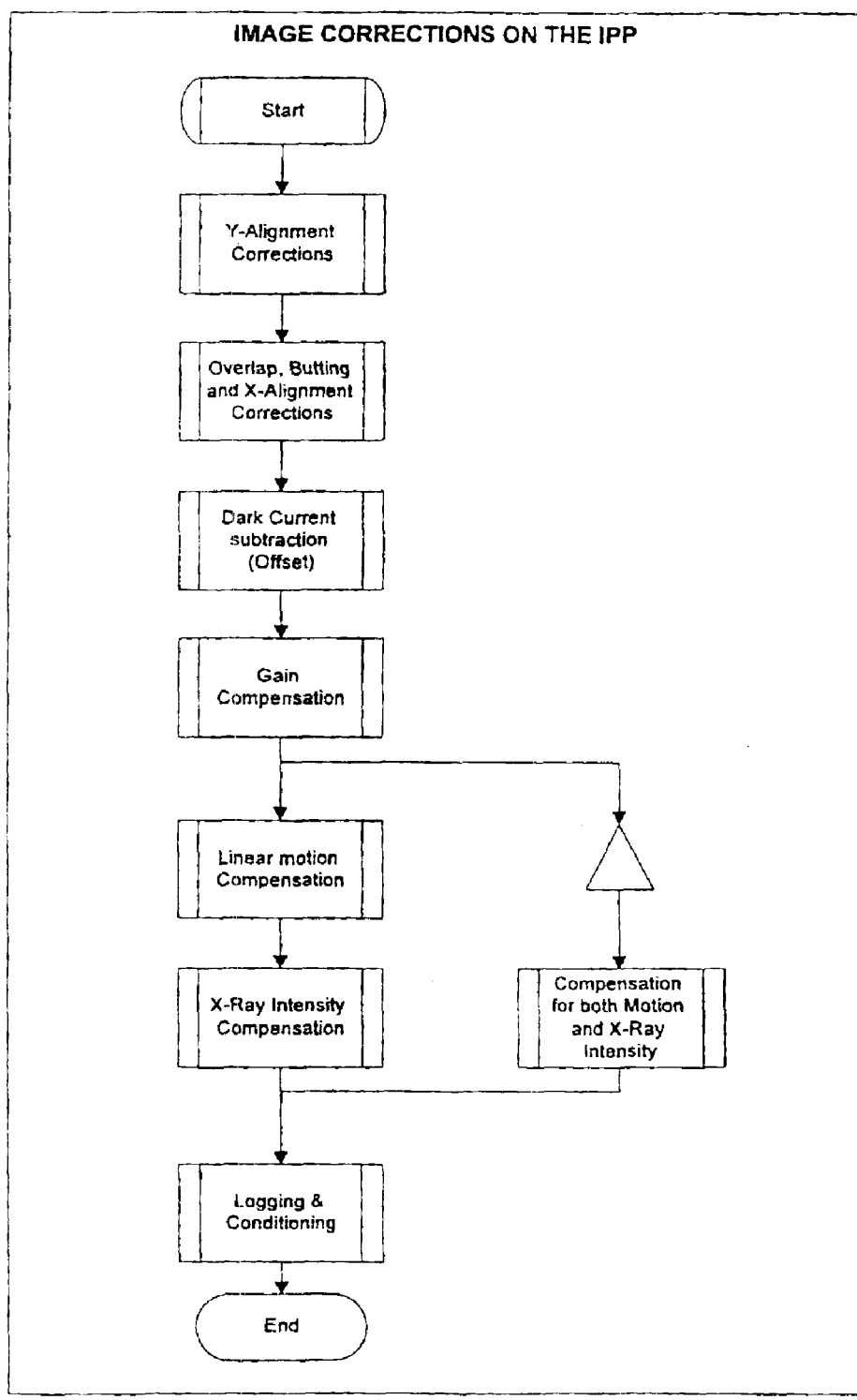

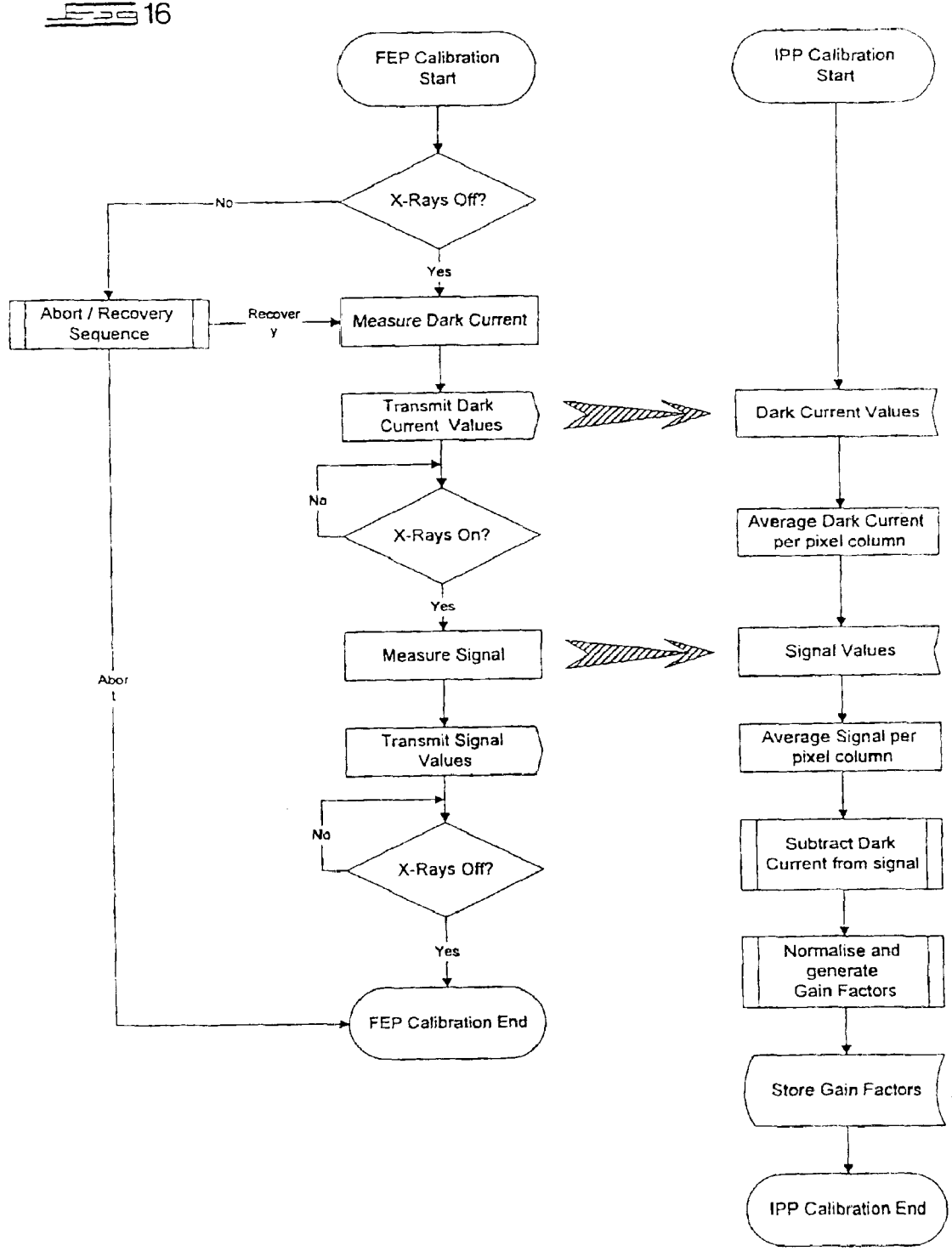

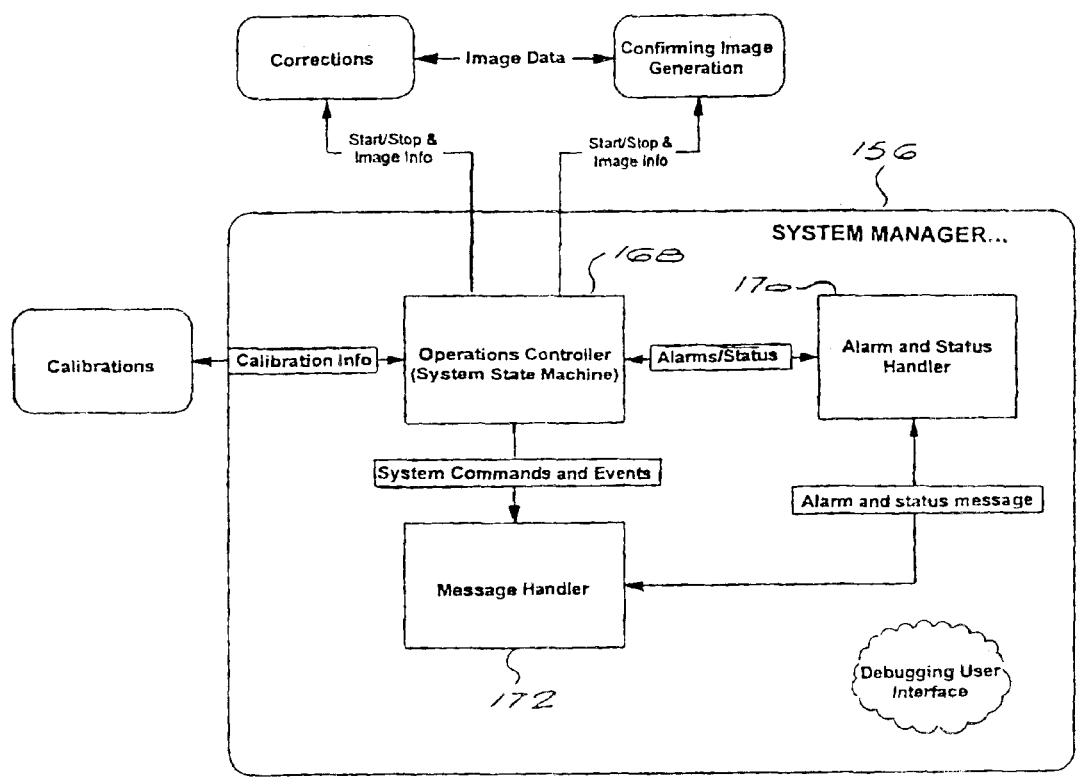

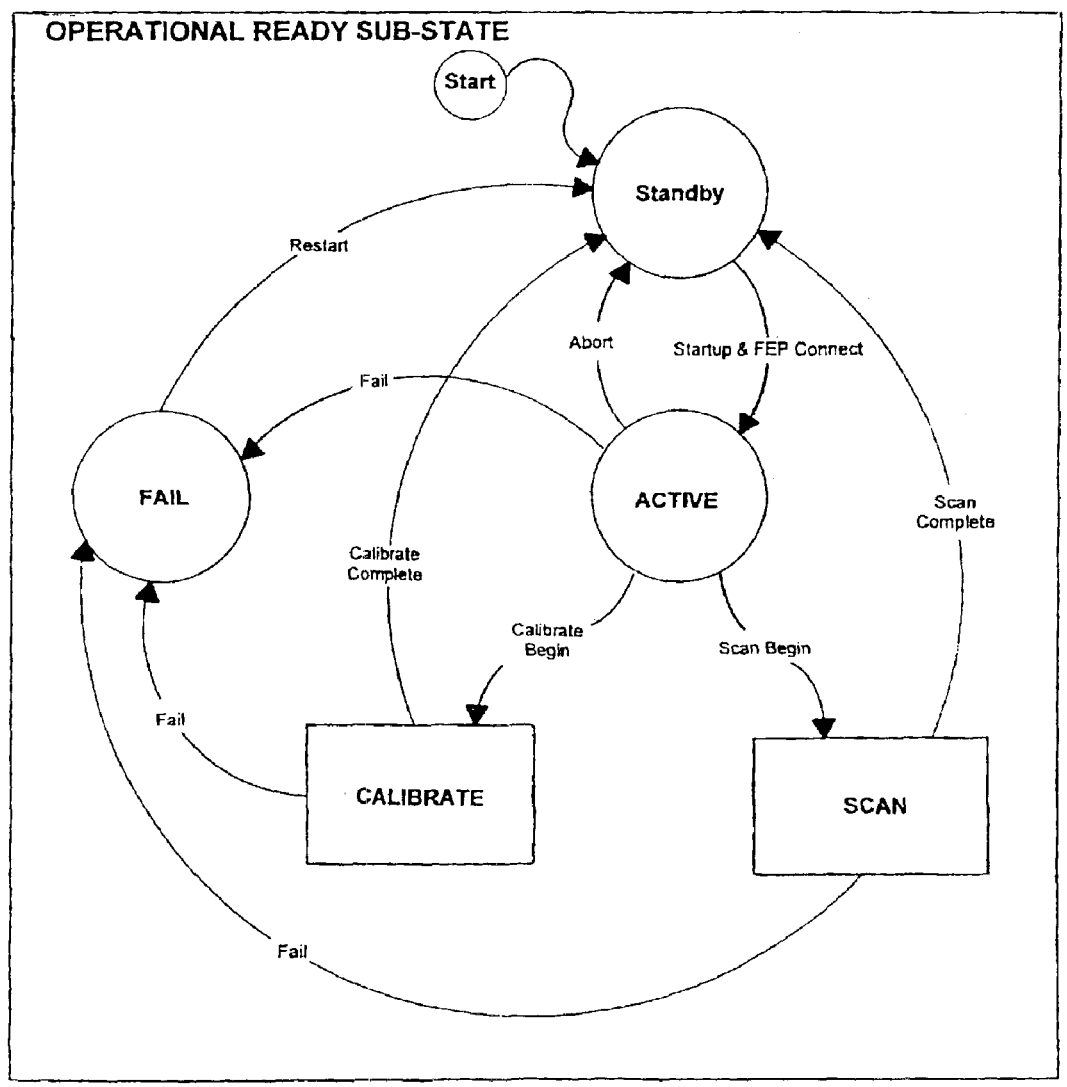

IMAGING APPARATUS

BACKGROUND TO THE INVENTION

THIS invention relates to imaging apparatus which can be used, for example, in radiological applications.

Conventional X-ray imaging apparatus is of limited versatility and is generally unsuitable for use in whole-body imaging of patients at a resolution sufficient for diagnostic purposes. South African patent no. 93/8427 describes a system which is designed to facilitate whole-body imaging of a subject in order to detect smuggled articles such as diamonds concealed on the person of the subject, while at the same time minimising the radiation dose received by the subject.

It is an object of the invention to provide an alternative apparatus which can produce images of medical diagnostic quality at relatively low radiation doses.

SUMMARY OF THE INVENTION

Imaging apparatus comprising:

a radiation source for generating an imaging beam;

a camera array comprising a plurality of cameras responsive to the imaging beam and arranged adjacent one another, each camera having an output for generating image signals;

drive means for moving the radiation source and the camera array relative to a subject;

signal processor means arranged to receive image signals from the data output of each camera and to generate composite image data therefrom;

memory means for storing the composite image data;

output means for displaying an image generated from the composite image data; and control means responsive to the image signals and/or the composite image data to control the operation of the drive means according to the intensity of the imaging beam.

The radiation source may be an X-ray source and the cameras comprise scintillators and associated charge-coupled devices for generating digital image data signals.

The camera array may be arranged so that fields of coverage of adjacent cameras overlap in a direction transverse to the direction of movement of the camera array, so that the camera array provides full coverage of an elongate imaging zone defined thereby.

In a preferred embodiment, each camera has an active area with a parallelogram shape, with adjacent ends of the respective active areas abutting, so that the coverage of adjacent cameras overlaps in a relatively narrow transition zone extending transversely to the direction of scanning.

The signal processor means preferably comprises a digital signal processor arranged to apply a compensation algorithm to the image data signals to compensate for relative misalignment or distortion of the cameras.

The compensation algorithm may be arranged to compensate for misalignment of each image pixel with respect to both x- and y-axes, the y-axis corresponding to the direction of scanning and the x-axis being transverse to the direction of scanning.

Preferably, the compensation algorithm is arranged first to compensate for errors in the positioning of pixels in the direction of the y-axis, and then in the direction of the x-axis to compensate for unexposed and overlapping pixels in the transition zones between the cameras.

The control means is preferably arranged to measure variations in the intensity of the imaging beam, and to generate drive control signals to vary the speed of the drive means, to maintain the effective intensity at a constant level.

The control means may be arranged to carry out intensity compensation by means of software correction of the image data signals using measured information regarding intensity fluctuations in the imaging beam.

The drive means may have an encoder associated therewith for generating clock signals related to the movement of the radiation source and the camera array, and the control means includes a clock conditioning circuit responsive to the clock signals to generate timing signals which are used to synchronise the imaging operation of the camera array with the movement thereof.

Alternatively, the control means may include a reference clock circuit which is used to generate timing signals for controlling both the operation of the drive means and the camera array, so that the imaging operation of the camera array is synchronised with the movement thereof.

Each camera preferably defines a plurality of imaging pixels. the outputs of at least some of the pixels being combined according to a predetermined scheme to improve the signal-to-noise ratio of the image signals.

In a preferred embodiment, the cameras are adapted to combine the outputs of pixels which are adjacent in the direction of movement of the radiation source and the camera array at the time of generation of the image signals.

The signal processor means is preferably adapted to process the image signals to combine the outputs of pixels which are adjacent in a direction transverse to the direction of movement of the radiation source and the camera array.

BRIEF DESCRIPTION OF THE DRAWINGS

The invention will now be described in more detail, by way of example only, with reference to the accompanying drawings in which:

FIG. 5 is a schematic illustration of the arrangement of the X-ray source;

FIG. 9 is a schematic illustration of an array of X-ray cameras of the detector of FIG. 7;

FIG. 10 is a schematic block diagram of a front end processor of the apparatus;

FIG. 11 is a block schematic diagram illustrating the hardware and software interfaces of an image pre-processor of the apparatus;

FIG. 12 is a block diagram of the image pre-processor;

FIG. 13 is a flow chart of the image correction performed by the image pre-processor, FIG. 14 illustrates one image correction performed by the image pre-processor;

FIG. 15 illustrates a second image correction performed by the image pre-processor;

FIG. 16 shows a flow diagram for determining coefficients to be used during compensation;

FIG. 17 is a schematic block diagram of the system manager of the image pre-processing circuitry; and FIG. 18 a schematic diagram illustrating the state modes of the image pre-processing circuitry.

DESCRIPTION OF PREFERRED EMBODIMENTS

Figure 1:
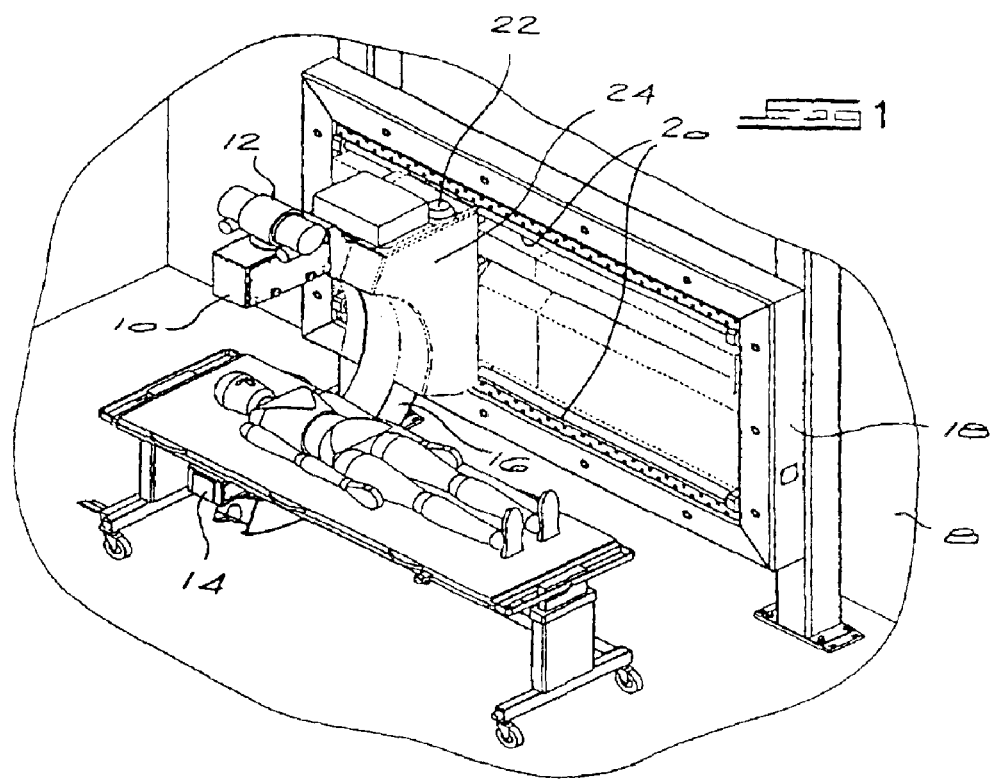
FIG. 1 is a pictorial view of imaging apparatus according to the invention.
Figure 2:
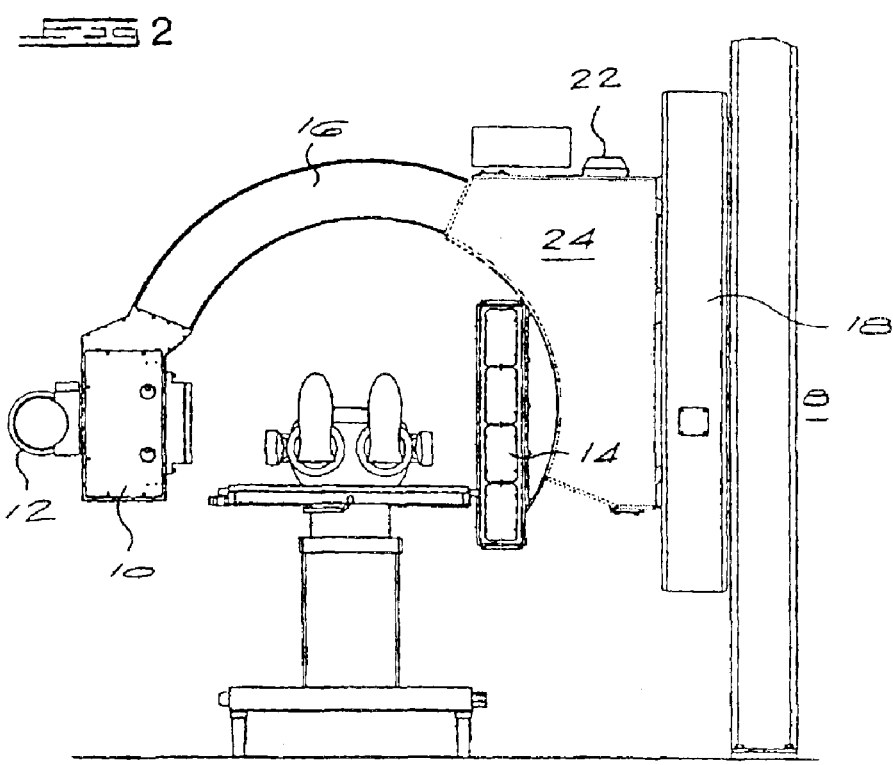
FIG. 2 is an end elevation of the apparatus of FIG. 1 showing a scanning arm thereof rotated through 90°.
Figure 3:
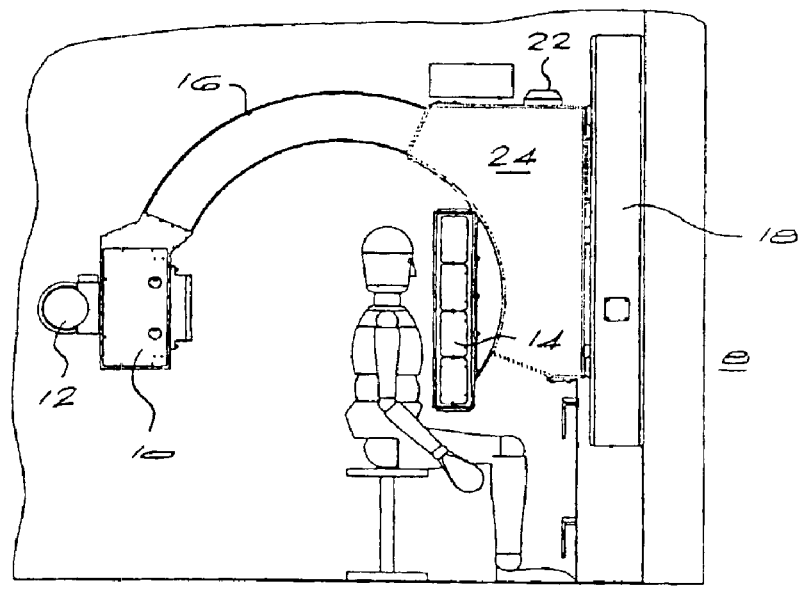
FIG. 3 is a similar view to that of FIG. 2, showing an alternative application of the apparatus.

FIGS. 1 to 3 show three different views of prototype X-ray imaging or scanning apparatus of the invention. The apparatus comprises a head 10 containing an X-ray source 12 which emits a narrow, fanned beam of X-rays towards a detector arrangement 14. The X-ray source 12 and the detector 14 are supported at opposite ends of a curved arm 16 which is generally semicircular or C-shaped.

A frame 18 mounted on a wall 8 or another fixed structure defines a pair of rails 20 with which a motorised drive mechanism 22 engages to drive the arm linearly back and forth in a first, axial direction of movement. In addition, the drive mechanism comprises a housing 24 in which the arm 16 is movable by the drive mechanism in order to cause the X-ray source and the detector to rotate about an axis parallel with the first direction of movement of the mechanism.

Figure 4:
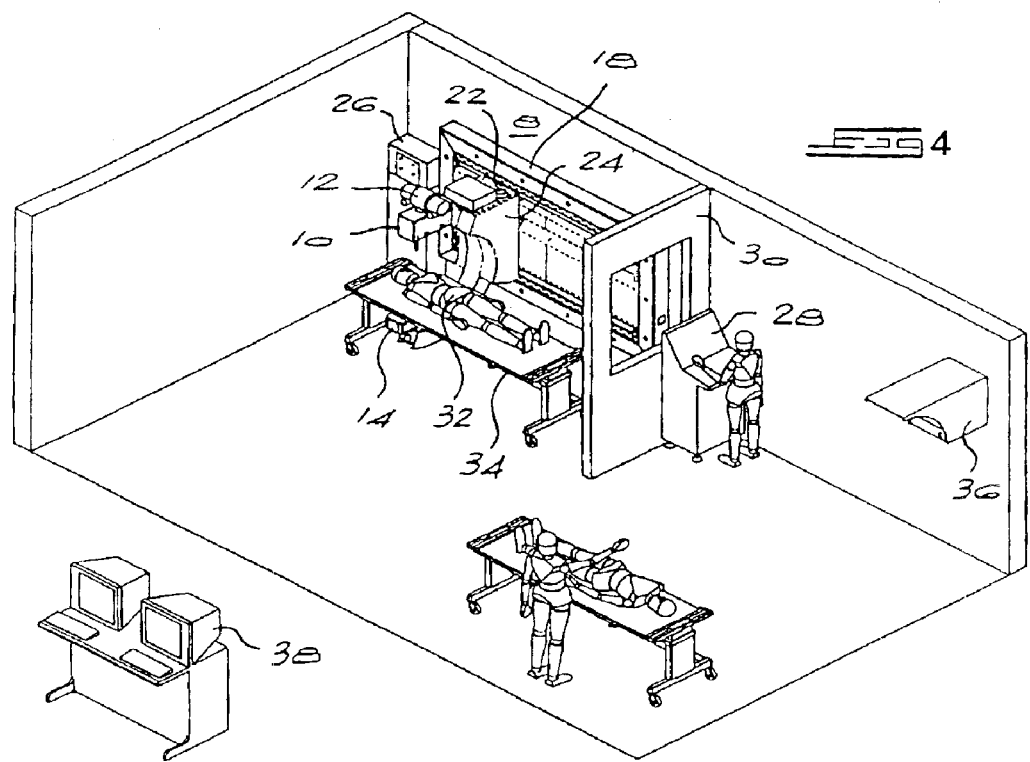
FIG. 4 is a pictorial view of a radiological installation incorporating the apparatus of the invention.

A typical application of the imaging apparatus of the invention is in a radiological installation, such as that illustrated in FIG. 4. The imaging apparatus is shown located in a corner of a room which may be a resuscitation area or trauma room of a hospital, for example. Alternatively, the apparatus may be located in a radiological department of a hospital or elsewhere.

Located adjacent to the imaging apparatus is a local positioning console 26, by means of which an operator can set up the required viewing parameters (for example, the angle of the arm 16, start and stop positions, and the width of the area to be X-rayed). A main operator console 28 is provided behind a screen 30 which is used by the operator to set up the required radiographic procedure. The imaging apparatus is operated to perform a scan of a subject 32 supported on a specialised trolley or gurney 34 (see below) and an image of the radiograph is displayed on a screen at the console 28, in order to allow the operator to judge whether a successful image has been acquired.

One or more high quality monitors 36 are provided for diagnostic viewing and are located so that attending clinical staff can study the radiographs being acquired. In addition, a console 38 is provided which forms part of a standard Radiological Information System which permits picture viewing and archiving.

The arrangement of FIG. 4 is designed for use in the resuscitation room of a trauma unit, in order to provide fast X-ray images of injured patients. Once a patient has been stabilised, he or she can conveniently be placed in position, scanned, and wheeled out for further treatment, with the resulting radiograph appearing on the diagnostic screen virtually instantaneously. Due to the low X-ray dose administered by the apparatus, the risk of radiation exposure to staff and patients is reduced.

The various functional aspects of the apparatus will now be described in greater detail.

In order to exploit the potential of the invention for rapid X-ray imaging, a special trolley 34 is provided which is height adjustable and which is provided with an electromagnetic clamping and location arrangement to secure it in position relative to the arm 16 of the scanning apparatus during operation.

Once the trolley has been locked in position, the arm 16 of the apparatus is rotated into the required position and is also locked into position electromagnetically. The shape of the arm defines a cavity which is sufficiently large to surround the body of a patient supported on the trolley 34.

With the arm 16 locked into position relative to the housing 24 of the drive mechanism and the trolley 34 also locked into position, the drive mechanism is operated so that the apparatus performs a horizontal linear scan. A narrow fanned beam of X-rays irradiates a thin strip across the width of the patient bed as the X-ray source and the detector move from the starting point to the end point of the scan.

A standard position of operation of the apparatus is with the X-ray source 12 uppermost in order to permit the taking of A-P (anterior to posterior) and P-A full body images. The arm 16 can be rotated through up to 90° for different radial/lateral views. The height adjustable trolley 34 is useful for pinpointing specific areas of interest. As an alternative to adjusting the height of the trolley, the height of the arm assembly could be adjusted instead. With the arm rotated through 90°, erect chest views are also possible, as indicated in FIG. 3.

In the prototype apparatus, the width or thickness of the X-ray beam (in the direction of scan) on the detector is determined by a thin slit collimator which is factory preset to less than 10 mm. Mounted in front of this slit is a second collimator that determines the length of the rectangular strip (transverse to the direction of scan) to be exposed to X-rays. This length is adjustable from a minimum of 100 mm to the full 680 mm field of exposure, in addition to a certain amount of offset from the bed centre line. A visible light source provided in the head 10 generates a thin beam, coincident with the X-ray beam, to illuminate the irradiated portion of the subject in use.

Referring to FIG. 5, the X-ray source consists of an X-ray tube, X-ray shutter, X-ray filter, coincident light source, collimator and X-ray beam width controller. The X-ray tube 100 generates X-rays and is powered by a high voltage power supply. The X-ray shutter 102 prevents exposure of the patient to X-rays in cases when the tube is provided with power but all the operational conditions are not met, for example during power-up or the ramping up of the scanner arm speed. It also acts as a safety interlock to the control system.

The X-ray filter 104 ensures that the spectrum is filtered to the correct "hardness" by removing "soft" or low energy X-rays which would be absorbed by the patient's body and not contribute to the quality of the image. A light source 106 and an X-ray translucent mirror 108 provide a light beam which is the shape of, and coincident with, the X-ray beam. This indicates the X-ray beam's size and position to the operator.

An X-ray collimator 110 blocks off the unwanted divergent X-rays which are detrimental to image quality, promote scatter and unnecessarily increase the amount of dose to the patient. The collimator is a thin slit in an X-ray opaque, material, which is located at a distance far enough from the X-ray tube to allow approximately a parallel beam of X-rays through. The percentage of nonparallel X-rays is determined by factors such as the slit's width, the slit's depth and the distance from the slit to the X-ray tube's focal spot. The image quality is improved in two ways by using the collimator. It effectively creates a parallel or collimated beam of X-rays and it reduces the instantaneous exposure area.

The degree of beam collimation specifies the angle of divergence of the X-ray beam, or the degree to which the X-rays are parallel. The non-parallel X-rays effectively cause parallax errors which in turn give rise to smear. The degree of collimation therefore determines the amount of image smear as a result of the scanning X-ray technique. The minimum resolution required in the scanning X-ray system determines the amount of smear that can be tolerated and hence the minimum degree of collimation.

A secondary result of the collimated X-ray beam is a very narrow (typically less than 10 mm) instantaneous exposure area. An image is produced through X-rays by irradiating an object and capturing the transmitted rays. The X-rays are differentially absorbed in the object as result of variations in thickness and densities throughout the object. However, a certain amount of the X-rays are scattered isotropically and do not travel straight to the detector. These scattered X-rays do not add to the information in the image, but are rather a source of noise. By utilising a very narrow instantaneous exposure area and correspondingly narrow detector, a minimum of these scatter X-rays are picked up by the detector, thereby reducing the noise in the image. This allows the X-ray dose to be reduced relative to large area exposures, while maintaining the necessary signal to noise ratio.

In some configurations of the apparatus, the useful X-ray beam thickness may be narrower than the actual detector thickness. This could cause unwanted scattered X-rays to be detected. In order to prevent this, a further collimator or post-collimator, situated between the detector and the patient, could be used to screen off these scattered X-rays, thereby further improving the signal to noise ratio of the system. Such a post-collimator can comprise two strips of high X-ray attenuating material, such as tungsten, placed on either side of the useful X-ray beam in such a way that any scattered X-rays do not reach the detector.

Figure 6A:
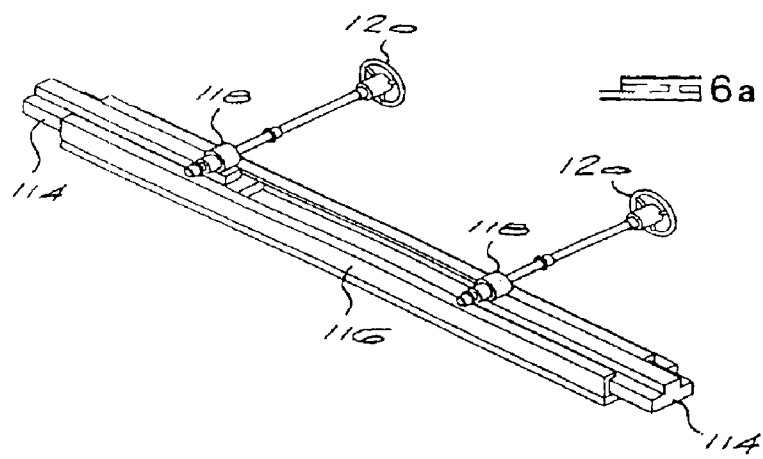
FIG. 6 is a schematic illustration of a beam width adjuster for the X-ray source.
Figure 6B:
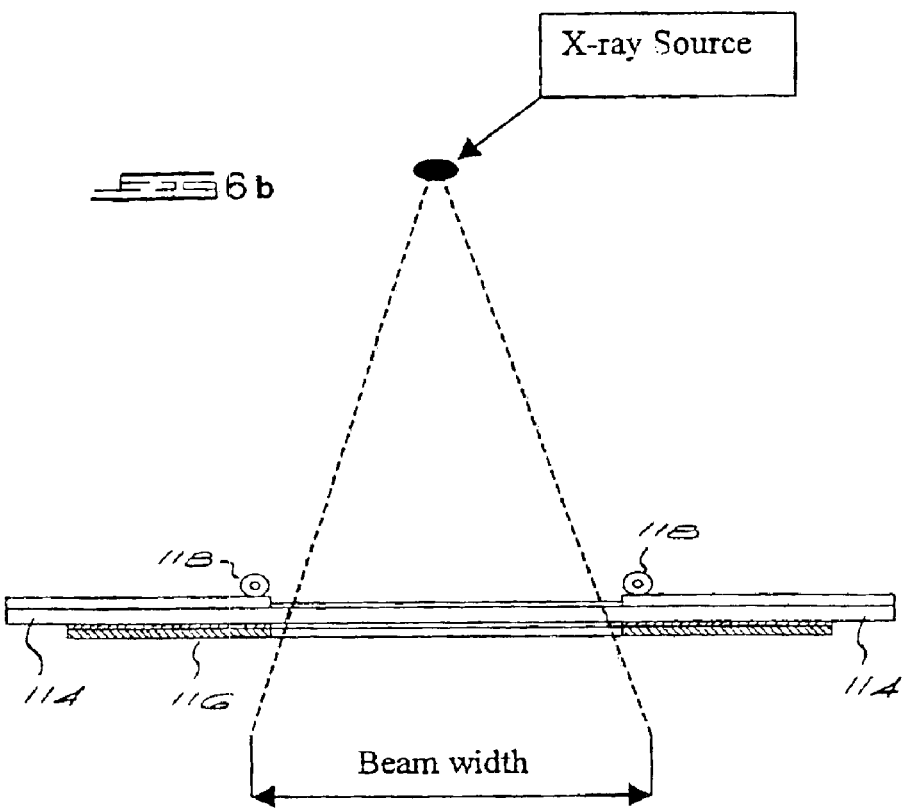
Figure 6C:
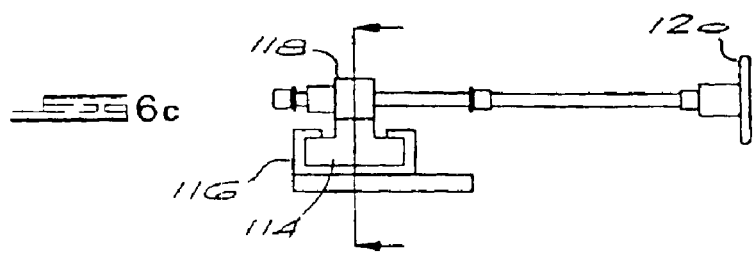

Control of the X-ray beam width is accomplished by means of a beam width controller or shutter mechanism 112, illustrated schematically in FIGS. 6a, b and c. The beam width controller fulfils similar functions to the collimator in improving image quality, reducing scatter and reducing unnecessary dose to the patient. The X-ray beam width controller 112 controls the width of the X-ray image as well as any offset from the centre of the beam. It is also useful to limit the beam width to the X-ray camera (situated in the X-ray detector, illustrated in FIG. 7) to avoid saturation. The prototype beam width controller consists of two geared bars or racks 114 manufactured from an X-ray opaque material and having a T-section. The racks 114 are slidable longitudinally in a channel 116 and are moved into and out of the beam by means of respective pinions 118, which can be connected to electrical motors or to knobs 120 as illustrated, for automated or manual movement, respectively. The exposure area's length can be adjusted from 100 mm up to any desired length (680 mm in the prototype).

Figure 7:
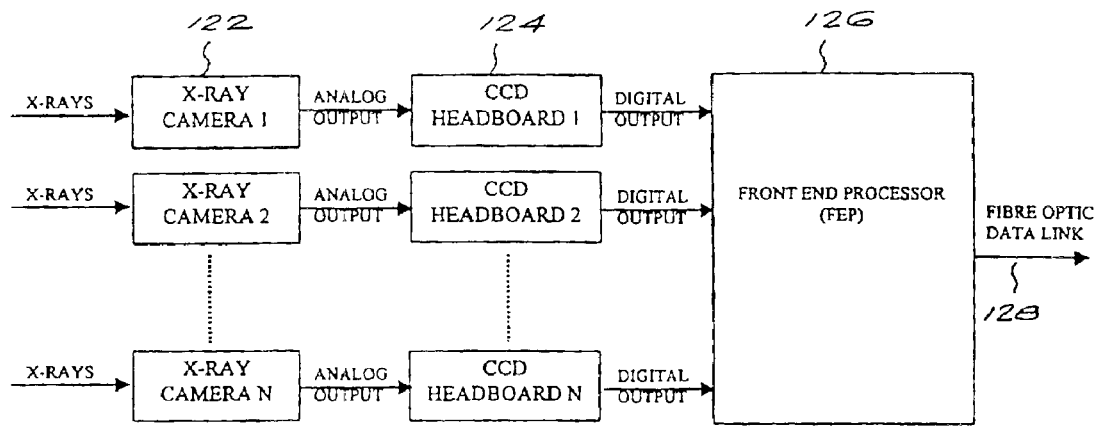
FIG. 7 is a schematic block diagram of the X-ray detector of the. apparatus.

The X-ray detector 14 is illustrated schematically in FIG. 7 and comprises a plurality of X-ray cameras 122, each with an associated CCD headboard 124. Charge Coupled Devices (CCD's) are effective at detecting radiation in the visible wavelength range and converting it to an analogue electronic output signal. They are less effective at detecting X-rays and are damaged by X-ray radiation. Scintillators are therefore employed to convert the X-rays to light. The scintillators cover the whole area over which the X-rays strike the camera. CCD's are limited in size and are extremely expensive. The image area is therefore covered by multiple CCD'S, the total number being determined by a cost vs. resolution trade-off.

The outputs of the respective CCD headboards 124 are fed to a front end processor 126 which has a fibre optic data link output 128. In the prototype, twelve CCD headboards 124 were interfaced to one front end processor 126. The front end processor (FEP) 126 is mounted in the C-arm 16 in close proximity to the CCD headboards, and connectors on the front end processor 126 are spaced to facilitate as short as possible an interface to the CCD headboards.

Figure 8A:
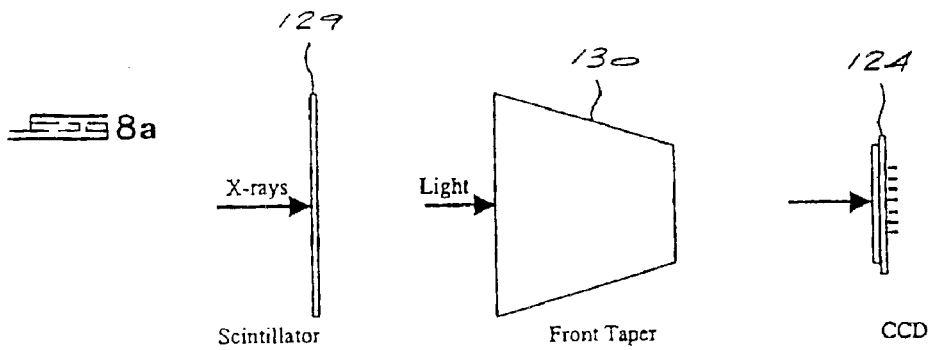
FIG. 8 is a schematic illustration of an individual X-ray camera of the detector of FIG. 7.
Figure 8B:
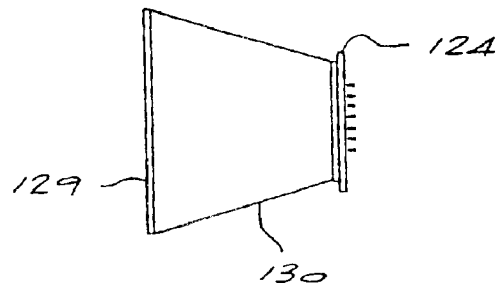

The arrangement of a single camera is illustrated schematically in FIGS. 8a and b. The camera comprises a scintillator 129, a fibre optic taper bundle 130 and the associated CCD headboard 124. Fibre optic taper bundles are employed in order to reduce the image size and project the image from the scintillator onto the discrete CCD'S (each camera has an active area which has a parallelogram shape in plan, so that the coverage of adjacent cameras overlaps in a direction transverse to the direction of scanning).

FIG. 9 shows the front face of the camera array schematically illustrating the parallelogram shape of each camera's active area and the resulting overlap in a narrow transition zone 174 transverse to the scan direction. Multiple cameras are butted together in order to obtain a composite detector which is approximately 700 mm wide. All the cameras have an identical parallelogram shape to ensure that the scanned image does not contain any blank areas. The gaps between the cameras are also minimised to approximately 50 micrometers in order to reduce the amount of information lost in the joints. The scanned area covered by each camera overlaps with the area scanned by the adjacent cameras to ensure that no information is lost. The overlapping images are combined into one image using software, once the data reaches the image pre-processor (described in detail below). Any other artefacts, such as image distortion or X-ray intensity fluctuations, can also be compensated for in the image pre-processor.

Each X-ray camera 122 detects X-rays which are transmitted through the patient and converts them to an analog electronic output signal. This output signal is amplified by the respective CCD headboard 124 which is mounted directly on the X-ray camera. The gain through the analog path is variable to enable compensation for variable signal intensity. The X-ray signal intensity may vary as a result of fluctuations in the scanning speed, ripple in the X-ray tube's power supply or imperfect X-ray tube parameters. This gain is controlled by control signals from a controller 132 (shown in FIG. 10).

After amplification and offset adjustment a standard correlated double sampling (COS) procedure is performed on the signal by a CCD analog processor (CAP) (not shown). The CAP further converts the analog CDS signal to a digital signal (containing the image data) of 14 bit depth, for example. The digital signal is routed via a ribbon cable to the front end processor 126.

The amplification, offset adjustment, CDS and digitisation should all be performed with low noise electronic circuits to minimise the amount of noise added to the image signal.

The CCD's are operated in a Time Delay and Integration mode in order to obtain maximum benefit from the drift scanning operation. The CCD pixels are clocked at a rate which corresponds to, and is derived from, the scanning speed of the C-arm 16. The digital timing signals are generated in the front end processor 126 in a Digital Programmable Block 134 (see FIG. 10). These timing signals are synchronized to the rest of the system by using the C-arm encoder clock signal 136, which is generated by the physical movement of the C-arm. Alternatively, if the movement of the arm can be controlled to be stable and predictable within the accuracy of the system, then the C-arm encoder-derived clock may be replaced with a precision reference clock circuit.

The C-arm encoder clock 136 needs to be conditioned depending on what format the output from the C-arm movement encoder will be, in order for it to be compatible with the digital signal levels used on the front end processor 126. A clock conditioning circuit 138 ensures this.

Feedback of the beam width is provided to the front end processor 126 and an image pre-processor (see FIG. 12). The front end processor 126 uses the beam width feedback to determine which cameras are exposed. The front end processor then activates only exposed cameras, thereby reducing the heat generated in the detector and the data rate on an optical fibre link to the image pre-processor. The image pre-processor uses the beam width feedback in the image processing calculations.

The CCD's of each CCD headboard consist of multiple rows and columns of pixels. Pixel rows are orientated perpendicular to the scanning direction. Electrons generated by X-rays are integrated in the pixel well during the time delay between the pixels' phase clocks, and are moved to the next row by the phase clocks. In each subsequent row additional electrons are generated by X-rays and the image exposure period is thereby lengthened. Image smear is prevented by clocking the pixels in accordance with the mechanical movement of the C-arm holding the X-ray source, as mentioned above. The signal is therefore integrated over the whole height of the X-ray fan beam and no X-ray signal is wasted.

Binning occurs where the values of two or more pixels are combined or added together. For example. two pixel by two pixel binning will produce a super-pixel that is the sum of four adjacent pixels. Vertical pixels (direction of scan, or y-axis) are binned in the CCD's 122, and horizontal pixels (perpendicular to direction of scan, or x-axis) are binned in the electronics of the front end processor 126 or the image pre-processor.

Binning of CCD rows is performed to increase the signal to noise ratio and to obtain the maximum required pixel size. If the rows were not binned it would increase the CCD readout noise present in the image. This binning of CCD rows is performed in the output registers of the CCD's 122 and is controlled by a programmable digital block 134.

It will be appreciated that, notwithstanding the above described specific configuration, the system may be designed in such a way that binning can occur flexibly either in the CCD or its readout hardware before any digitisation occurs, or once digitised, by software. The binning process may take place in combinations of rows or columns.

Although the front end processor 126 has many functions, three performance related specifications are critical to the final product. These are the speed at which the image information can be read out of the CCD, the data rate between the front end processor 126 and the image pre-processor, and the signal to noise ratio of the system. In a prototype system, the fastest scanning speed was found to be ten seconds for a full body scan (1800 mm). Each CCD must have its contents cleared, digitised and multiplexed at the scanning rate. The data rate between the front end processor and the image pre-processor will be determined by the smallest binned super-pixel which is a 2×2 binned pixel (see above for an explanation of pixel binning). This translates to a data rate of 147 Mbits per second, for all twelve channels.

Referring now to FIG. 10, the front end processor 126 comprises a digital programmable block 134 which consists of one or more FPGA's and the required memory.

The programmable digital block 134 samples the 14 bit digital signal from the CCD headboards. Binning up to the specified number of columns (typically between 1 and 5) is performed on the digital signal. Combined with the binning of rows in the CCD, as explained above, this gives rise to super-pixels with increased signal to noise ratio, which still maintains the pixel-size required for optimum resolution.

The programmable digital block 134 also generates CCD drive signals. These signals are level shifted on the CCD headboards to the appropriate levels to drive the CCD. The CCD operating voltages are generated in an external power supply. The CCD drive signals and operating voltages are then fed to the CCD headboards through a suitable cable.

The controller 132 mainly controls the different modes of operation of the front end processor 126 and also serves a built-in-test purpose, in terms of which monitors voltage levels and the basic functions on the processor PCB. The test status is reported back to the user interface through an interface 142, which could be an RS232C interface, for example. The controller also controls the different configurations of the programmable digital block 134. This is done by configuring the FPGA's differently each time a different mode of operation is required. This is necessary when different scanning speeds are selected and to perform alignment correction on the data. Feedback from the X-ray beam width control and the shutter are also fed to the controller 132. The controller 132 would typically be implemented using a microprocessor.

The X-ray intensity feedback signal is converted to a digital signal by an A/D converter 144. This signal is appended to each line or horizontal row of image data which is sent to the image pre-processor.

The circuit includes an oscillator 146. The oscillator output is a clock frequency which is very stable over a time period of one scan. The clock signal from the C-arm encoder is compared to this frequency. The result of the comparison indicates the variation in speed from the C-arm. This result is also appended to the each horizontal row of image data sent to the image pre-processor. The image pre-processor uses the intensity and speed variation information appended to each line to correct for the uneven illumination due to variations in the speed of travel of the C-arm. The oscillator also clocks the electronic circuits when the C-arm is not moving.

The image pre-processor is used to convert the image data output of the front end processor 126 into a form which can be displayed on a video monitor. The signal from the front end processor is a multiplexed data signal generated from the twelve individual data output signals from the respective CCD headboards 124. The overall block diagram illustrating the image pre-processor's hardware and software interfaces is shown in FIG. 11, while FIG. 12 is a schematic diagram of the image pre-processor, which is typically implemented in a personal computer 152.

As shown in FIGS. 11 and 12, the fibre optic data link output 150 of the front end processor 126 (see FIG. 10) is connected to a databus and fibre optic interface controller circuit 154 which converts the optical signals back to a digital electronic form. The signals are fed via the personal computer's databus to a random access memory (RAM), for processing by either the standard microprocessor or a dedicated digital signal processing (DSP) circuit. Once in RAM, the image correction task manipulates, corrects and converts the digital data into a form which can be transmitted to a diagnostic viewing station 36 via the database interface library 164.

The image pre-processor (IPP) consists of seven main functional blocks. Four of these control or provide access to interface points, whilst the other three provide the core functionality of the IPP. Referring to FIG. 11, these items are the IPP system manager 156, which controls the state and mode of the IPP. An image correction and enhancement task/thread 158 performs all the image corrections and enhancements. A confirming image generation task/thread 160 generates a confirming image, which is sent to the operator console 28. A front end processor (FEP) serial communications manager 162 handles the serial interface to the front end processor 126. This interface could be a standard RS232C link. The databus and fibre optic interface controller 154 handles the set up of the fibre optic interface and, depending on what driver support is provided by the manufacturer, handles the functionality to read data from this interface. A database interface library 164 handles all the interface requirements to an image database server and the diagnostic viewing stations 36. Finally, an interface to the operator console 166 handles the interface to the operator console 28.

The image pre-processor (IPP) processes the image data and corrects this data for imaging artefacts. The following performance factors are critical to the final product and the achievement of the IPP's main purpose:

FEP/IPP Fibre Data Link—The smallest binned superpixel is at least a 2×2 pixel binning. This translates to a data rate of 147 Mbits per second, for all cameras. The data link is able to sustain this transfer rate during the scan operation, and transfer this data into the IPP system memory in real-time.

Correction speed—The image is corrected as close to real time as possible. The correction algorithms ensure that a corrected and a confirming image is available to the operator at the operating console 28 and the diagnostic monitor 36 as soon as possible.

Image Size—The IPP keeps at least one copy of the full image in memory whilst performing the correction algorithm, and requires enough memory to do so.

Now described in detail are the image corrections performed on the images by the image pre-processor. These corrections are performed to compensate for the artificial elements that are added to a picture during digital capture and display. They are also aimed at removing artifacts caused by the butting of the cameras and the fibre optic tapers. The image corrections must be performed in a specific order, which is determined by the effect expected from a specific correction. A flow chart of the image corrections is shown in FIG. 13.

A standard sequence of corrections is:
1. y-alignment
2. x-alignment
3. CCD dark current subtraction (dc-offset subtraction)
4. signal normalisation (gain compensation)
5. compensation for scan speed variations
6. compensation for x-ray intensity fluctuations
7. scaling of image (for example, logarithmic)

Certain of the corrections may be left out of the sequence if their contribution to image quality is not warranted by the expense of processing speed.

The first correction performed is y-alignment. This correction compensates for the slight difference in positioning of the cameras in the x-y plane. A separate y-alignment value is defined for each pixel instead of for each camera. As the fibre optic tapers can cause bow distortion of the image, defining a separate value for each pixel instead of for each camera allows the bow distortion to be compensated for, hence the need for separate values for each pixel as opposed to per camera. This translates to a vertical shift of image values. This correction should take care of the problem illustrated in FIGS. 14(a) and (b). A facility is also provided to allow the user to edit the compensation values of the final curve.

The second correction is a butt or x-alignment correction. This can only be performed once the pixels have been appropriately aligned in the y-direction and it therefore follows the y-alignment. The fibre optic tapers used are parallelogram in shape which results in an overlap of pixels at the join of two tapers. There is also some portion of the CCD that is not covered by a taper. This results in dark or unexposed pixels on either side of the tapers. The unexposed pixels lying at the ends of each taper will be eliminated in the front end processor 126 during binning. Hence the correction software need only concern itself with the overlapped values created by the butting.

Suppose that camera n and camera n+1 overlap by $t_{n0}$ pixels, as shown in FIG. 9. The overlap is compensated for by adding the values of the overlapping pixels ie. the first $t_{n0}$ pixels of camera n+1 are added to the last $t_{n0}$ pixels of camera n. This caters for the problem illustrated schematically in FIG. 15.

The next two corrections are standard gain and offset compensations. Once again a separate offset and gain value is used per column and not per camera.

The dark current level or dc offset value is determined during calibration before the scanning of each image starts, to compensate for temperature drift in the CCD. This is done by obtaining an image without exposing the detector with X-rays. An average signal level is calculated for each image column and this constitutes the dc offset value. Each column in the image is then corrected for the dc offset by subtracting the corresponding dark current offset value for that column from each pixel in that column.

The gain mask is also determined during calibration. This mask does not need to be determined during every scan, but rather during scheduled calibration sessions. The raw gain mask is obtained for every X-ray energy, by exposing the camera with an uninterrupted beam of X-rays and averaging the image per column. Thereafter the offset mask is subtracted from the gain mask and the result becomes the final gain mask. Each column in the image is normalised for the corresponding gain by dividing each pixel by the corresponding value in the gain mask. FIG. 16 shows the flow diagram for determination of the coefficients to be used during compensation.

Similar to the gain mask compensation is the compensation for scan speed variations and for X-ray intensity fluctuations. Variations in the scan speed and X-ray intensity effectively cause gain variations per row in the image. The change in gain is proportional to the change in speed or intensity and the image can be normalised per row with respect to these variations.

The above steps are carried out as follows:
Step 1: Measure the dark current with the X-rays off.
Step 2: Acquire image gain when the X-rays are turned on.
Step 3: Subtract the dark current from the image.
Step 4: Normalise the image using the gain factors determined from the gain mask, X-ray intensity and speed variations.

The final correction of the image is the logging of the corrected value. This is necessary because X-ray attenuation is exponential. The required log values are obtained by means of a predefined look-up table which is generated during initialisation time and remains in memory for usage thereafter. The log values are calculated in such a way as to provide for conditioning of the image as well as logging it. The values in the look-up table would range from 0 to 16384 if a 14 bit range is utilised. These corrections must be performed as fast as possible in order to adequately cope with the demands of a trauma unit.

The algorithms used to perform the abovementioned corrections have been highly optimised to improve the performance and speed of the system. The algorithms have been implemented as a multi-threaded process, with multiple tasks running concurrently. This process consists mainly of three tasks:

1. The main task receives image information and only begins performing the abovementioned corrections after the maximum number of rows that could be misaligned has been received. (The reason for waiting for the maximum number of rows that could be misaligned before starting the corrections is to ensure that the linear shifts performed by the y-alignment do not go out of scope.) This thread is given critical priority to ensure that the corrections are performed as fast as possible.

2. A contrast enhancement task begins processing the image as soon as there are corrected rows available from the main task This task performs the so-called "unsharp mask" operation (basically a contrast enhancement, grey-scale compression and edge enhancement algorithm) on the corrected rows. This task makes use of a kernel, which is a square matrix, and convolves this matrix over the corrected rows to produce an "unsharp mask" image. This image forms the basis of the confirming image displayed on the operator's console.

3. A reduction task reduces the image produced by either of the above tasks to generate a pictogram of the radiograph (image) taken. The reduction factor is normally set to 12, but is dynamically configurable depending on the size of the image taken.

Tasks 2 and 3 above are used interchangeably depending on the customer's requirements. Normally an "unsharp mask" image is generated as a confirming image, and a reduced version of this is used as a pictogram for later selection on the database. This setup is interchangeable, allowing a reduced radiograph to become a confirming image and an "unsharp mask" version of this then becoming the pictogram.

Apart from these main tasks, there are miscellaneous tasks which perform the following functions:

a) Conditioning of the "unsharp masked" image. Under conditioning the following is understood:
   floating point values are converted into 8-bit integer values,
   range is adjusted for optimal viewing scale (adjusted to fit into 8-bit scale according to max/min values) and erratic data (eg. negative values) that does not contribute to the picture is removed (adjusted to max/min values).

b) Removal of unexposed columns (these are created by clocking all the columns in the CCD's regardless of whether or not they lie within the scope of the collimator settings, because CCD's cannot be read out only partially).

c) The transmission of both the corrected image and confirming image to the database and the operator console respectively.

Illustrated in FIG. 17 in more detail is the system manager 156, which is responsible for controlling the state, mode and operation of the image capture system.

The system manager 156 consists of three processes:

An operations controller 168, which manages the general operation of the image capture system. The operations controller also controls the correction, calibration, and confirming image generation processes;

An alarm and status handler 170 which manages the alarm and status database as well as the alarm history; and A message handler 172 which manages all messages that are posted to the IPP mailbox, and posts all responses to the relevant mailboxes.

FIG. 18 shows the image pre-processor state machine as controlled by the system manager 156. After initialisation, the system manager remains in a disconnected state until the operator console 28 and the image database server connect, and establish the relevant communication channels. The image pre-processor is then available and ready for use. The front end processor 126 does not need to be connected, or be communicating at this phase. This allows the front end processor to enter a power saving mode.

It is the responsibility of the image pre-processor to begin communication with the front end processor, so that It may wake-up from the power saving mode and begin activation and preparation for a scan. The operator console will notify the image pre-processor that a scan is about to begin, and that the image pre-processor needs to prepare for a scan. The image pre-processor immediately communicates over the serial link to the front end processor, thus waking up the front end processor from the power-saving mode and causing it to connect and communicate with the image preprocessor. Once a valid response has been received from the front end processor, the image pre-processor enters the active state waiting for a scan-activate notification from the operator console. The image pre-processor then undergoes the scan process. On termination, it reverts to the standby state.

Thus it can be seen that the invention provides an alternative apparatus which can produce images of medical diagnostic quality at relatively low radiation doses.

What is claimed is:

1. Imaging apparatus comprising:
   a radiation source for generating an imaging beam;
   a camera array comprising a plurality of cameras responsive to the imaging beam and arranged adjacent one another, each camera comprising rows and columns of pixels and having an output for generating image signals;
   drive means for moving the radiation source and the camera array relative to a subject;
   signal processor means arranged to receive image signals from the data output of each camera to process the image signals and to generate composite image data and to determine the imaging beam intensity therefrom; wherein the signal processor means further comprises a digital signal processor arranged to apply a compensation algorithm to compensate for misalignment of each image pixel with respect to both x- and y-axes, with the compensation algorithm arranged first to compensate for errors in the positioning of pixels in the direction of the y-axis, which axis corresponds to the direction of scanning, and then in the direction of the x-axis, which axis is transverse to the direction of scanning, thereby to compensate for unexposed and overlapping pixels in the transition zones between the cameras and to compensate for relative misalignment or distortion of the cameras;

memory means for storing the composite image data;

output means for displaying an image generated from the composite image data; and control means responsive to the image signals and/or the composite image data to control the operation of the signal processor means according to the intensity of the imaging beam;

the camera array arranged so that fields of coverage of adjacent cameras overlap in a direction transverse to the direction of movement of the camera array, so that the camera array provides full coverage of an elongated imaging zone defined thereby.

2. Imaging apparatus according to claim 1 wherein the radiation source is an x-ray source and the cameras comprise scintillators and associated charge-coupled devices for generating digital image data signals.

3. Imaging apparatus according to claim 1 wherein each camera has an active area with a parallelogram shape, with adjacent ends of the respective active areas abutting, so that the coverage of adjacent cameras overlaps in a relatively narrow transition zone extending transversely to the direction of scanning.

4. Imaging apparatus according to claim 1 wherein the control means is arranged to measure variations in the intensity of the imaging beam, and variations in the speed of the drive means, and to correct the image signals and/or composite image data accordingly.

5. Imaging apparatus according to claim 1 wherein the control means is arranged to carry out intensity compensation by means of software correction of the image data signals using measured information regarding intensity fluctuations in the imaging beam.

6. Imaging apparatus according to claim 1 wherein the drive means has an encoder associated therewith for generating clock signals related to the movement of the radiation source and the camera array, and the control means includes a clock conditioning circuit responsive to the clock signals to generate timing signals which are used to synchronise the imaging operation of the camera array with the movement thereof.

7. Imaging apparatus according to claim 1 wherein the control means includes a reference clock circuit which is used to generate timing signals for controlling both the operation of the drive means and the camera array, so that the imaging operation of the camera array is synchronized with the movement thereof.

8. Imaging apparatus according to claim 1 wherein each camera defines a plurality of imaging pixels, the outputs of at least some of the pixels being combined according to a predetermined scheme to improve the signal-to-noise ratio of the image signals.

9. Imaging apparatus according to claim 8 wherein the cameras are adapted to combine the outputs of pixels which are adjacent in the direction of movement of the radiation source and the camera array at the time of generation of the image signals.

10. Imaging apparatus according to claim 9 wherein the signal processor means is adapted to process the image signals to combine the outputs of pixels which are adjacent in a direction transverse to the direction of movement of the radiation source and the camera array.

* * * * *